United States Patent
Medoff et al.

(10) Patent No.: US 7,044,951 B2
(45) Date of Patent: May 16, 2006

(54) FRACTURE FIXATION DEVICE IN WHICH A FIXATION PIN IS AXIALLY RESTRAINED

(75) Inventors: Robert J. Medoff, 30 Aulike St., Suite 506, Kailua, HI (US) 96734; Lars G. Tellman, Kyrkogatan 6, S-23011 Falsterbo (SE)

(73) Assignees: Robert J. Medoff, Kailua, HI (US); Lars G. Tellman, Falsterbo (SE); David Medoff, Valencia, CA (US)

( * ) Notice: Subject to any disclaimer, the term of this patent is extended or adjusted under 35 U.S.C. 154(b) by 356 days.

(21) Appl. No.: 10/073,825

(22) Filed: Feb. 11, 2002

(65) Prior Publication Data
US 2002/0147452 A1   Oct. 10, 2002

Related U.S. Application Data

(60) Provisional application No. 60/268,100, filed on Feb. 12, 2001.

(51) Int. Cl.
*A61B 17/56* (2006.01)
(52) U.S. Cl. ........................................ 606/71
(58) Field of Classification Search .................. 606/71, 606/69, 70, 72, 73, 76, 77, 61
See application file for complete search history.

(56) References Cited

U.S. PATENT DOCUMENTS

| | | | | |
|---|---|---|---|---|
| 2,526,959 A | * | 10/1950 | Lorenzo | 606/66 |
| 4,794,918 A | * | 1/1989 | Wolter | 606/69 |
| 5,006,120 A | * | 4/1991 | Carter | 606/69 |
| 5,127,914 A | | 7/1992 | Calderale et al. | 606/65 |
| 5,300,074 A | | 4/1994 | Frigg | 128/67 |
| 5,931,839 A | * | 8/1999 | Medoff | 606/69 |
| 6,508,819 B1 | * | 1/2003 | Orbay | 606/69 |

* cited by examiner

*Primary Examiner*—Pedro Philogene
(74) *Attorney, Agent, or Firm*—Ladas & Parry LLP

(57) ABSTRACT

A fixation device for fixing a fracture in a bone structure, in which a fixation pin adapted for penetrating into a stable fragment of a bone structure across a fracture has an end extending from an unstable fragment of the bone structure and a fixation plate adapted for being secured to the stable bone fragment distally from the end of the fixation pin. The fixation plate is engageable with the end of the pin to prevent the pin from backing out of the unstable bone fragment while providing restraint against movement of the pin in the plane of the plate. The end of the pin extending from the unstable bone fragment is engaged an opening in the end of the fixation plate and restrained thereat.

27 Claims, 12 Drawing Sheets

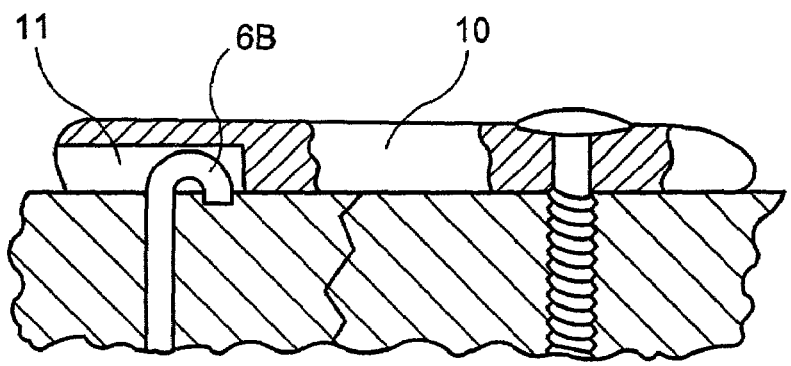
F I G. 11
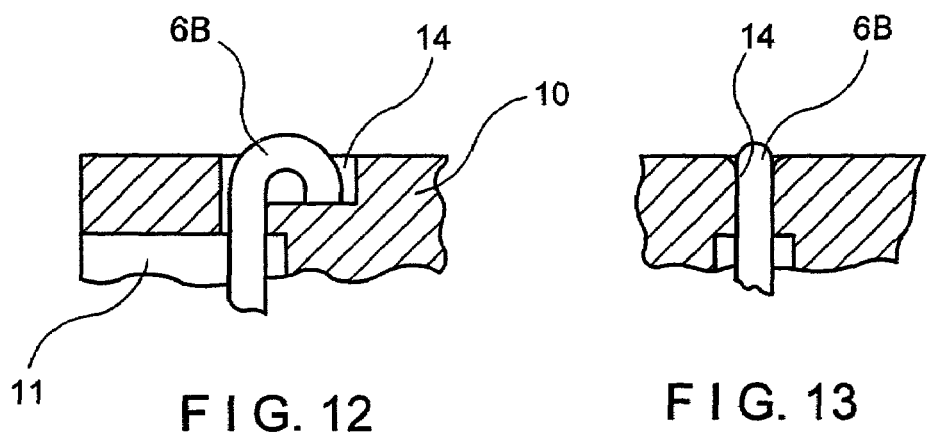
F I G. 12
F I G. 13
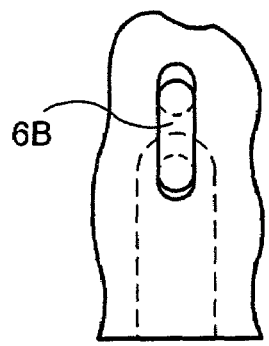
F I G. 14

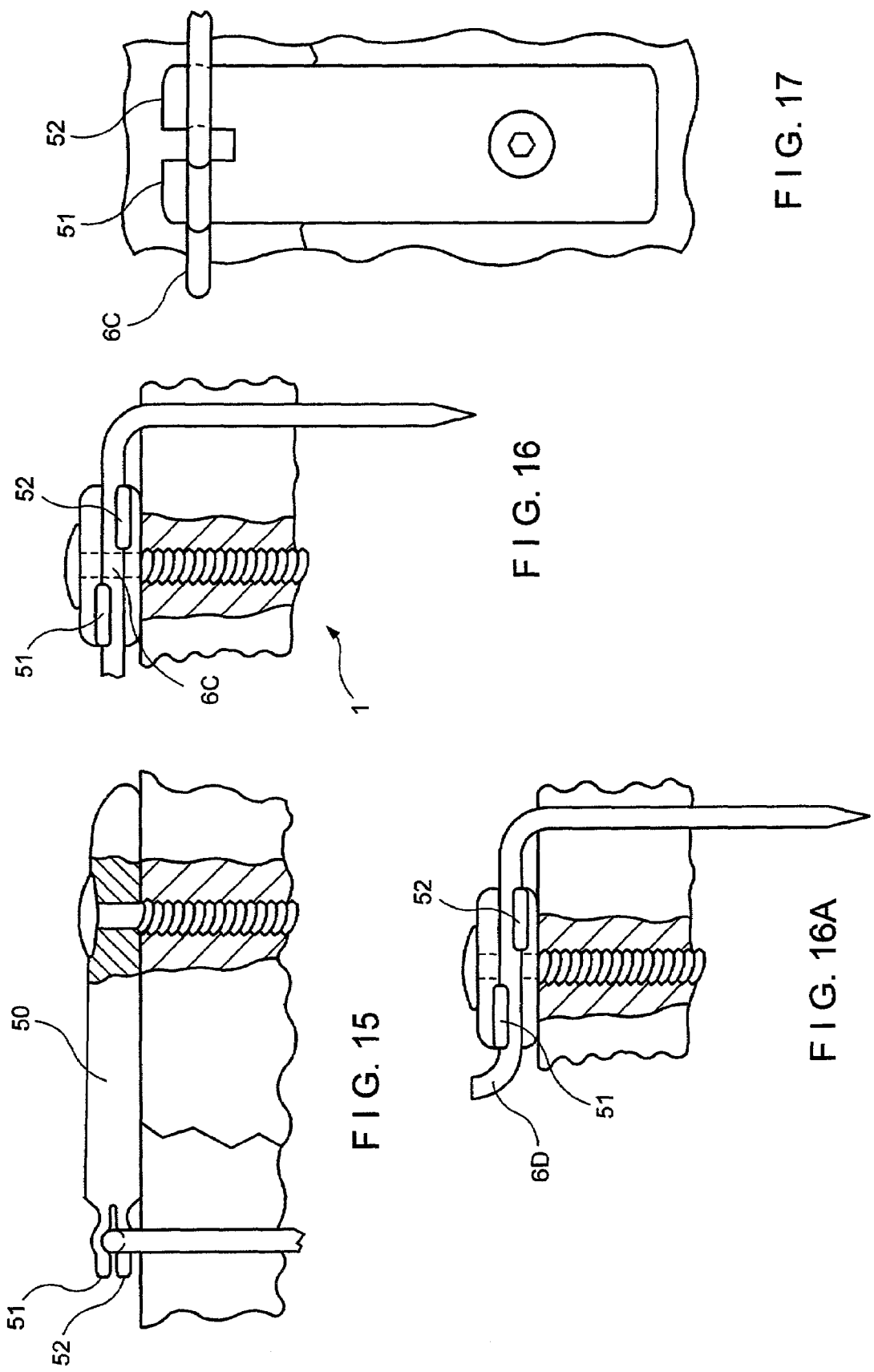

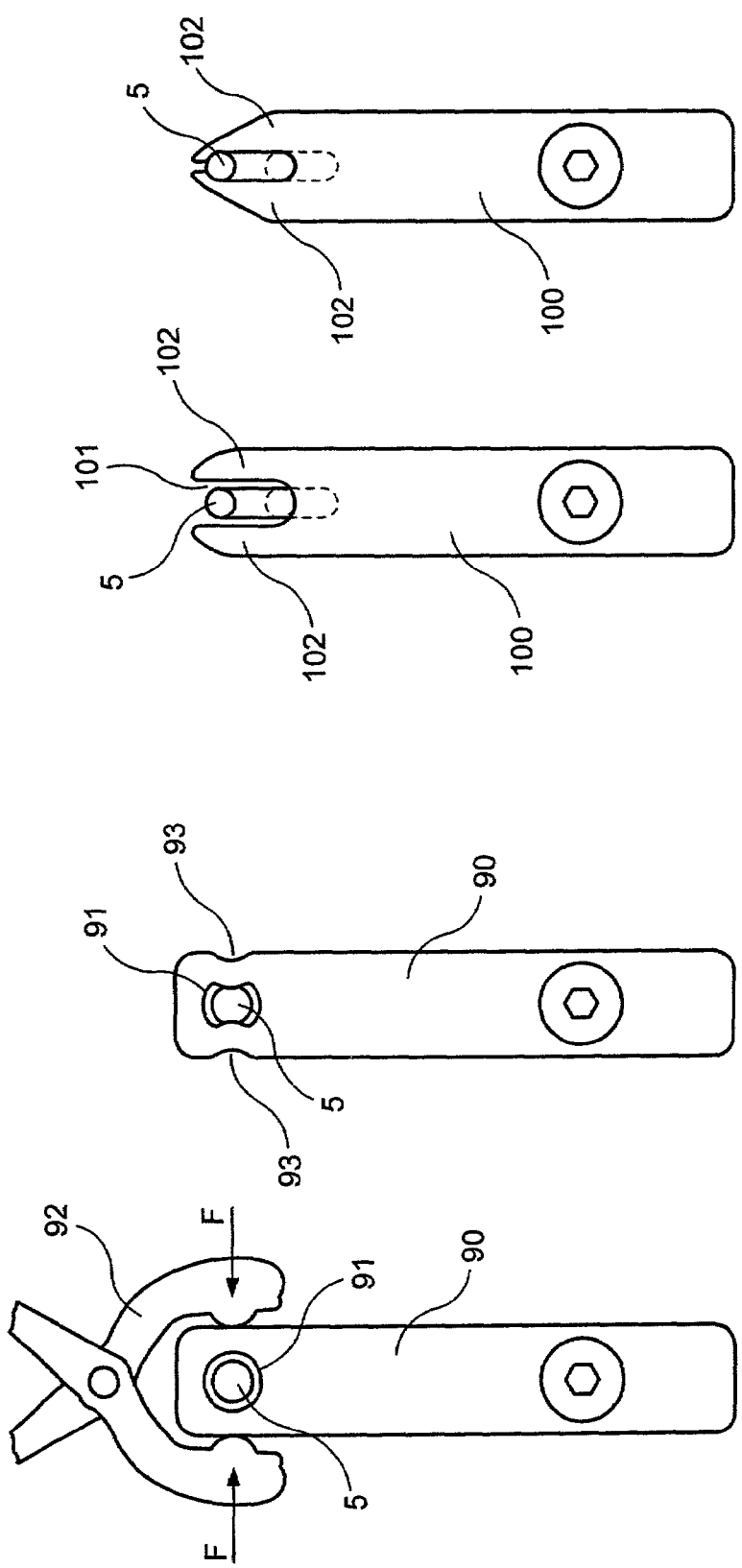

FRACTURE FIXATION DEVICE IN WHICH A FIXATION PIN IS AXIALLY RESTRAINED

This application claims the benefit of Provisional Application No. 60/268,100, filed Feb. 12, 2001.

FIELD OF THE INVENTION

The invention relates to a fixation device for fixing a fracture in a bone structure and more particularly to a fixation pin for penetrating an unstable bone fragment for being secured to a stable bone fragment, the pin having an end which extends out of the bone structure and is restrained by a fixation plate.

The invention also relates to a method of fixing a bone fracture utilizing such a pin and plate.

BACKGROUND AND PRIOR ART

In my earlier U.S. Pat. No. 5,931,839, there is disclosed an implantable fixation device which comprises a K-wire or pin for fixation of a bone fracture and a fixation plate for engaging the end of the pin which extends from the bone structure. In the patent, the protruding end of the pin is engaged in a hole in the fixation plate such that the pin is free to axially travel in the hole. In order to prevent separation of the pin from slipping out of from under the hole in the plate, the end of the pin can be bent while preserving the axial sliding capability of the pin in the hole in the plate.

Single K-wire fixation of bone fragments does not provide secure fixation, since the K-wire is secured only at a single end that can be at a considerable distance from the fracture site. The fixation or pin plate provides fixation of the K-wire at a second site, but has the disadvantage of requiring the K-wire to be bent over the edge of the plate or into an adjacent hole in the plate. This step requires backing out of the K-wire and is cumbersome and can lose reduction.

In addition, current pin plate designs allow the pin to back out with motion of the fracture. This can lead to abrasion of adjacent soft tissue structures and even tendon rupture.

SUMMARY OF THE INVENTION

An object of the invention is to provide a fixation means providing constraint of the K-wire adjacent to the site of entry into the unstable fracture fragment or at a position close thereto.

A further object of the invention is to secure the top of the protruding end of the K-wire to prevent translational movement of the K-wire as well as to prevent backing out of the wire into the soft tissues.

Another object of the invention is to provide a bend in the K-wire prior to placement of the fixation plate so that the K-wire need not be withdrawn from the bone, simplifying the procedure.

In accordance with the above and further objects of the invention, the fixation device for fixing a fracture in a bone structure comprises a fixation pin adapted for penetrating through an unstable bone fragment of the bone structure across a fracture into a stable bone fragment, the pin having one end secured to the stable bone fragment and an opposite end extending out from the unstable bone fragment, and a fixation plate adapted for being secured to the stable bone fragment at a distance from the outwardly extending end of the fixation pin. The outwardly extending end of the fixation pin is smooth and the fixation plate is engageable with the end of the pin to prevent the pin from backing out of the unstable bone fragment while providing restraint against movement of the pin in the plane of the plate.

In further accordance with the invention, the end of the pin is bent and the fixation plate has means for engaging the bent end of the fixation pin.

According to one feature of the invention, the means for engaging the bent end of the fixation pin is constituted by a lower surface of the fixation plate which bears against the bent end of the fixation pin to restrain the pin with respect to the bone structure.

According to a further feature of the invention, the means for engaging the bent end of the fixation pin comprises a groove in the fixation plate for receiving the bent end of the pin.

A further feature of the invention is that the bent end of the fixation pin extends substantially parallel to the underlying bone structure.

According to another embodiment of the invention, the end of the pin is straight and it is engaged in an opening in the plate and secured in the opening by crimping the plate.

According to another embodiment of the invention, the pin is cut where it protrudes through a hole or groove in the plate and welded in situ to the plate to prevent it from backing out.

In another aspect of the invention, a method is provided for fixing the fracture which method comprises inserting a fixation pin into the bone structure across a fracture and leaving an end of the pin extending from the bone structure, securing a fixation plate to the bone structure at a distance from the extending end of the fixation pin, and engaging the fixation plate with the portion of the pin to prevent the pin from backing out of said bone structure while providing restraint against movement of said pin in the plane of the plate.

BRIEF DESCRIPTION OF THE FIGURES OF THE DRAWING

FIG. 11 shows another embodiment of the engagement of the fixation plate and the K-wire.

FIG. 12 shows a further embodiment of the engagement of the fixation plate and the K-wire.

FIG. 13 is an end view of FIG. 12.

FIG. 14 is a plan view of FIG. 12.

FIG. 15 shows a further embodiment of the engagement of the fixation plate and the K-wire.

FIG. 16 is an end view of FIG. 15.

FIG. 16A is similar to FIG. 16 and shows a modification thereat.

FIG. 17 is a plan view of FIG. 15.

FIG. 28 is a top plan view of FIG. 27 in a preliminary stage of assembly of the fixation plate and pin.

FIG. 29 shows FIG. 28 after completion of the assembly.

FIG. 30 shows a modified embodiment of FIG. 29 in a preliminary stage of assembly.

FIG. 31 shows FIG. 30 after completion of assembly.

DETAILED DESCRIPTION

Figure 1:
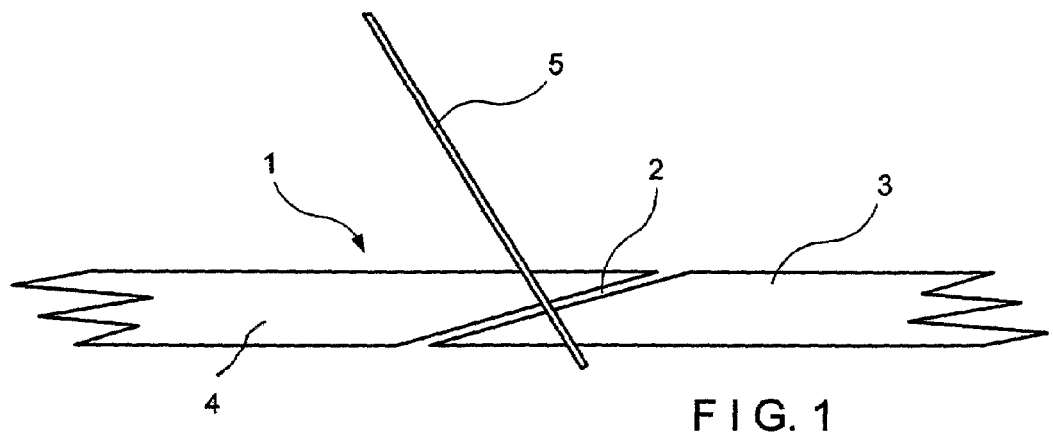
FIG. 1 is a side elevational view showing a conventional K-wire placed in bone structure.
Figure 2:
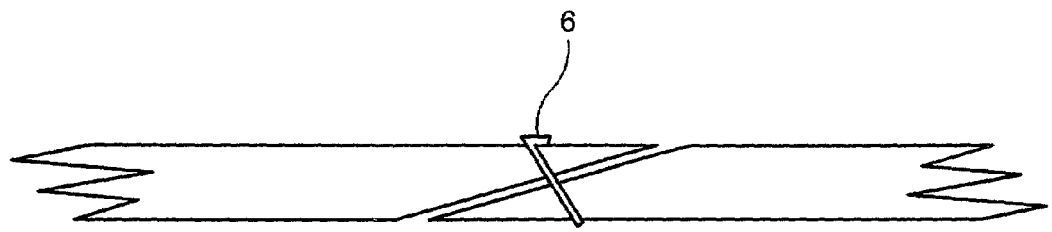
FIG. 2 shows an end of the K-wire bent over at the entry site of the pin in the bone structure.

Referring to FIG. 1 therein is seen a bone structure 1 having a fracture 2 therein forming a stable bone fragment 3 and an unstable bone fragment 4 on opposite sides of the fracture 2. In order to provide fixation of the unstable bone fragment 4 to the stable bone fragment 3, a K-wire or pin 5 is inserted through the unstable bone fragment 4 across the fracture 2 into the stable bone fragment 3. The end of the pin 5 which engages in the stable bone fragment 3 can be smooth or threaded to insure its anchorage in the stable bone fragment. After the pin 5 has been secured in the bone structure and the fracture 2 has been reduced, the part of the pin 5 extending from the anterior surface of the bone structure is severed and bent to form a bent portion 6. The bent portion 6 is bent at an angle so that the bent portion 6 will be substantially parallel to the superficial surface of the bone structure 1 and be capable of engagement thereon as shown in FIG. 2. In order to secure the protruding end of the pin 5, a fixation plate 10 is fixedly secured to the stable bone fragment 3 by bone screws 11 or equivalents thereof, such as pins, wires, blades, staples, brackets and the like as well known in the art. The fixation plate 10 is provided with a groove 12 in its lower surface at an end of the plate so that the bent portion 6 of the pin can be engaged in the groove 12 to secure the pin against translational movement in the plane of the plate and to prevent the pin from backing out of the bone structure by an axial movement of the pin out of the bone structure.

The term "pin" used herein refers to pins, wires, nails with or without heads, and a thin screw or the like. The difference between "pins" and rigid elements, such as screws, blades and the like is in the thickness or diameters thereof. In order to simplify the description, the term "pin" is intended to cover all of the above and similar devices in the description herein flexible enough to allow the surgeon to bend the pin at the site where it exits from the bone. The term K-wire describes a smooth, fully or partially threaded wire element of uniform diameter that is stiff enough to drill or impact into bone.

Figure 3:
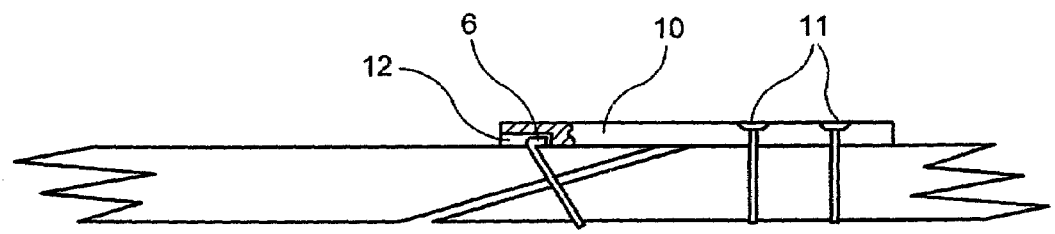
FIG. 3 shows, partially broken away and in section a locking or fixation plate secured to the bone structure.
Figure 3A:
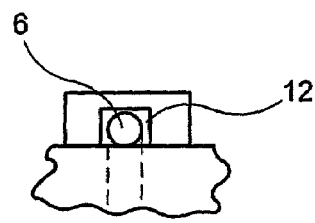
FIG. 3A is an end view from the left in FIG. 3 from the left in FIG. 3 showing the engagement of the fixation plate and the K-wire.
Figure 4:
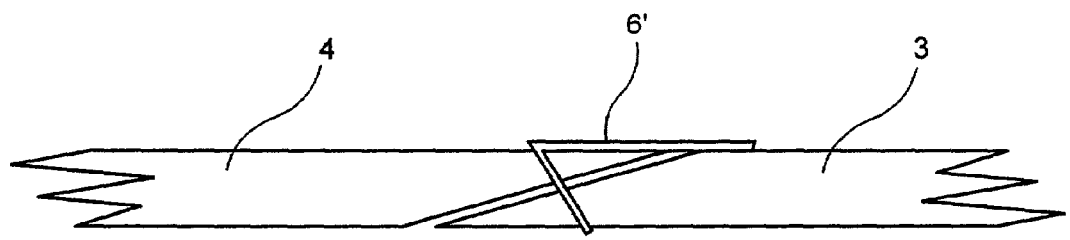
FIG. 4 is a modification of the bent portion of the K-wire in which the bent portion extends beyond the fracture in the bone structure.

Referring to FIG. 4, herein the arrangement is similar to that in FIG. 2 except that the bent portion 6' is of greater length and extends over the fracture 2 to adjoin the stable bone fragment 3. The fixation plate 10' is similar to that in FIG. 3 but is shortened to receive only the end of the bent portion 6'. In this embodiment, the end of the bent portion 6' of the fixation pin is at a distance from the site of entry of the pin into the unstable bone fragment.

Figure 5:
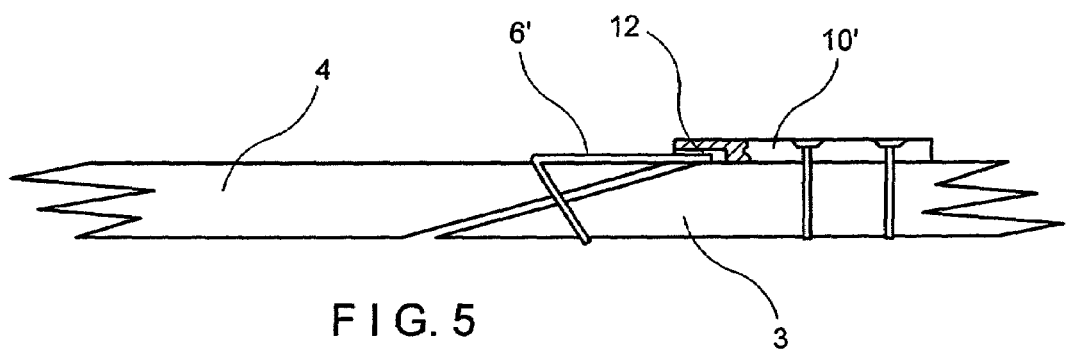
FIG. 5 shows another embodiment of the fixation plate engaging the bent portion of the K-wire.

In FIGS. 3 and 5, the groove 12 is formed in the fixation plate at the lower surface of the fixation plate and the groove opens at the tip end of the plate to capture the end of the pin.

Figure 6:
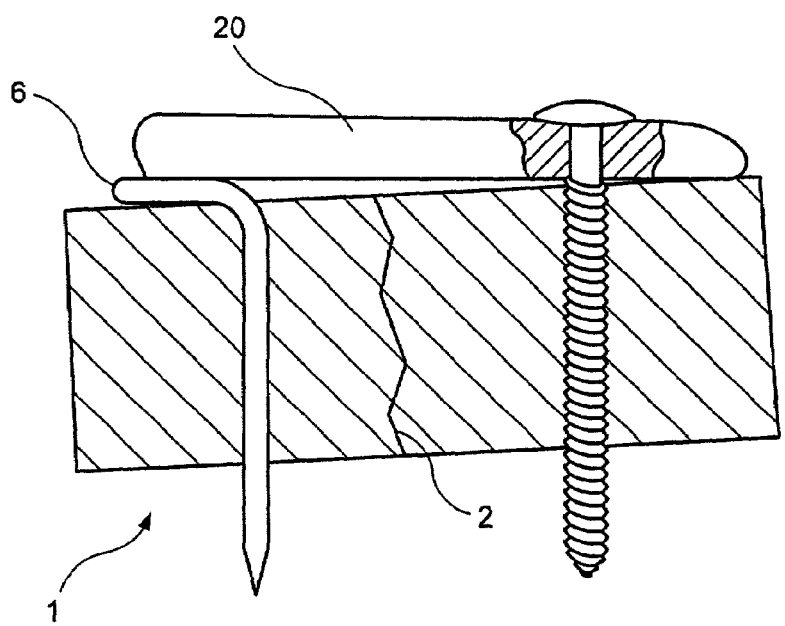
FIG. 6 shows another embodiment of engagement of the fixation plate and the bent portion of the pin.

FIG. 6 shows an embodiment in which fixation plate 20 is applied directly on the bent portion 6 of the pin without any groove. Effectively, the plate 20 clamps the bent portion 6 of the pin against the superficial surface of the bone fragment 4 of the bone structure 1.

Figure 6A:
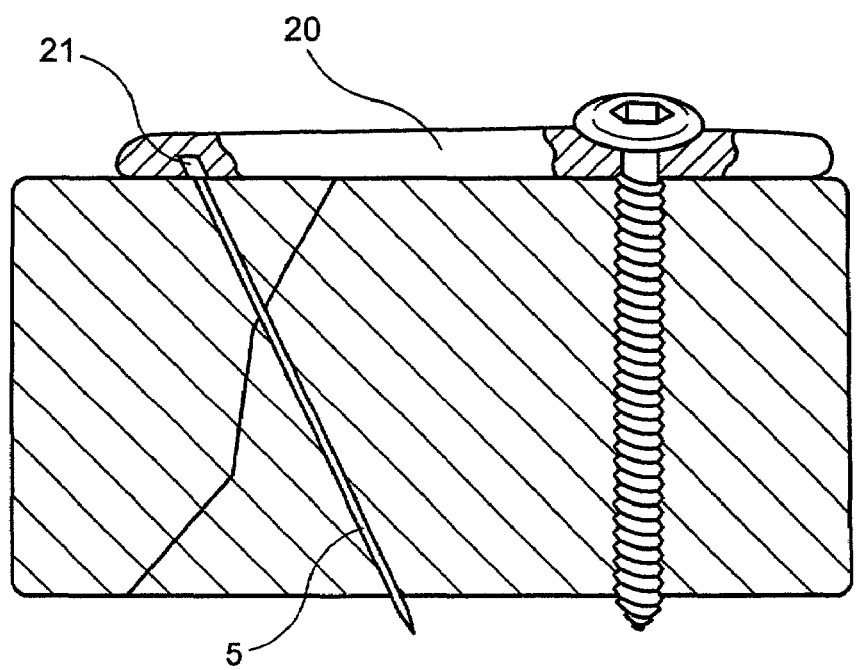
FIG. 6A shows another embodiment of engagement of the fixation plate and the end of the pin.

In a modification shown in FIG. 6A, the end of the pin 5 is not bent and the underside of the plate 20 is formed with a groove or dimple 21 on its undersurface to engage the protruding end of the pin and prevent the pin from sliding underneath the plate. Since the groove or dimple 21 is confined within the undersurface of the plate, the pin is prevented from backing out of the bone structure by the plate.

Figure 7:
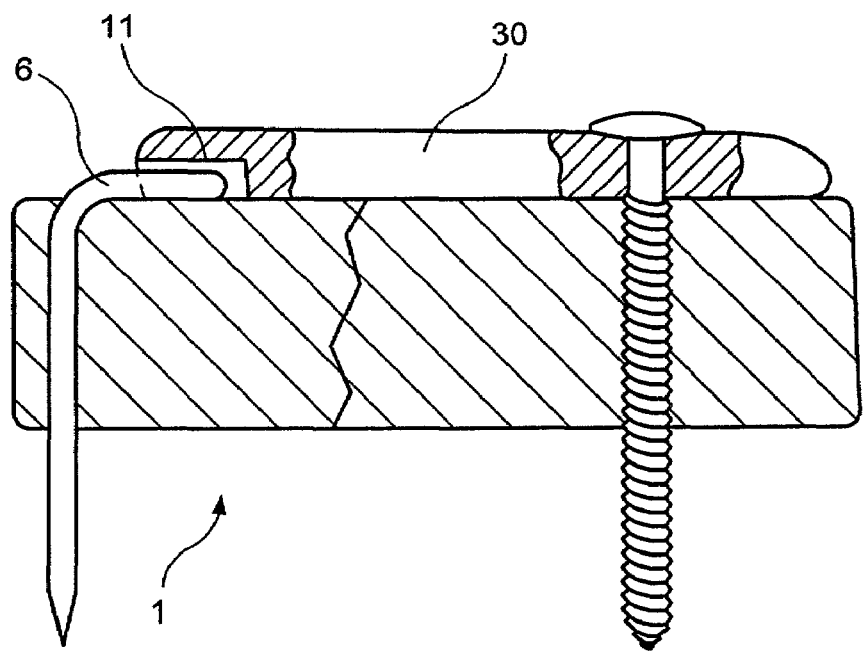
FIG. 7 shows another embodiment of the engagement of the fixation plate and the K-wire.

FIG. 7 is a combination of the embodiments in FIGS. 1, 3 and 5 in that the bent portion 6 is engaged in the groove 11 of the fixation plate 30. However, the pin is inserted into the bone structure at a site outside the fixation plate but in proximity thereto.

Figure 10:
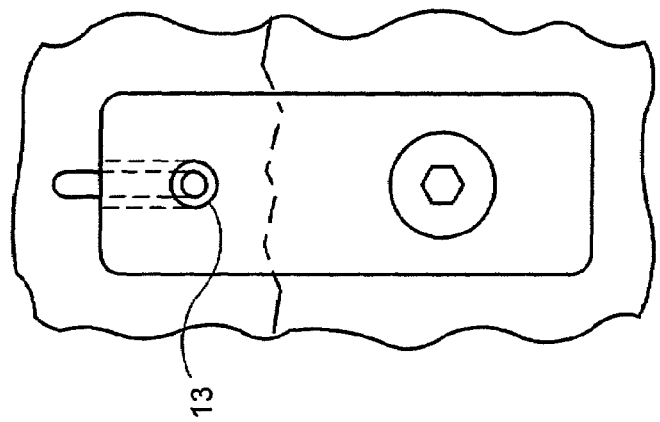
FIG. 10 is a top plan view of FIG. 8.
Figure 9:
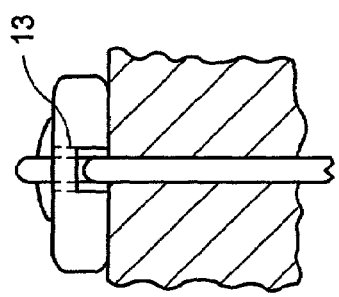
FIG. 9 is a sectional view taken along line 9—9 in FIG. 8.
Figure 8:
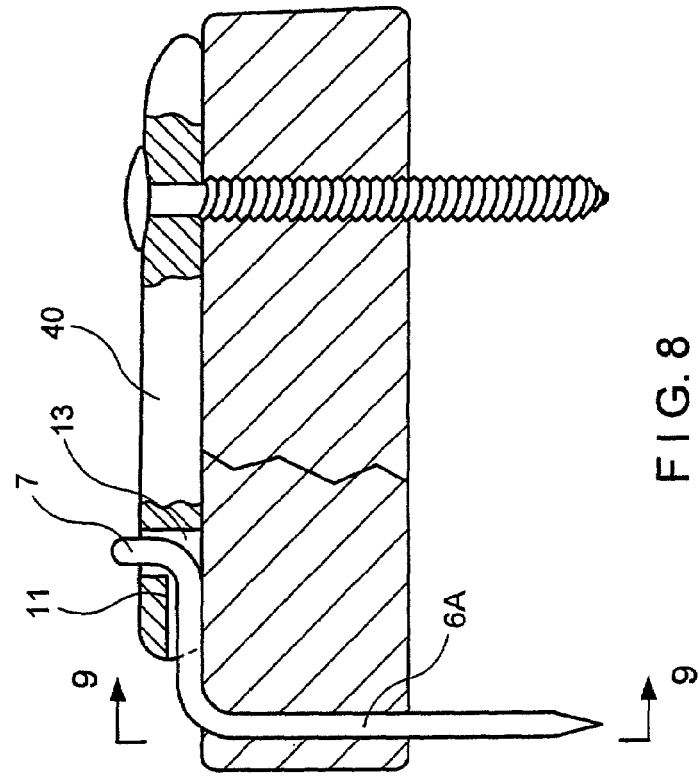
FIG. 8 shows a further embodiment of the engagement of the fixation plate and the K-wire.

FIGS. 8–10 show a modification in which a hole 13 is provided in the fixation plate 40 and connects with the groove 11 to receive a second bend portion 7 formed at the end of the pin 6A. This embodiment provides a secure engagement of the pin to further prevent the pin from slipping out from under the fixation plate.

FIG. 11 shows another modification in which the pin is bent in a U-shape at 6B instead of lying flat as shown in FIG. 2. The engagement of the bent portion 6B in the groove 11 and the restraint provided thereby is the same as in the previously described embodiments.

FIGS. 12–14 show a modification of the embodiment in FIG. 11 in which an elongated groove 14 is provided in the upper surface of the plate. The groove 14 is slightly undersized with respect to the diameter of the pin, so that the bent portion of the pin is frictionally gripped in the groove 14 thereby restraining the pin in the fixation plate.

FIG. 15 shows a fixation plate 50 having longitudinally extending tabs 51 and 52 thereon in transversely spaced relation as shown in FIG. 16. The tabs are at different levels and face inwardly in opposite directions to engage the bent portion 6C of the fixation pin from above and below to grip the bent portion. In this embodiment, the bent portion of the pin extends transversely of the fixation plate and the engagement of the bent portion 6C with the fixation plate takes place transversely of the entry site of the fixation pin into the bone structure 1.

FIG. 16A is similar to FIG. 16 except that the terminal end of the pin is bent at 6D to restrain the pin and prevent the pin from slipping out from the tabs.

Figure 20:
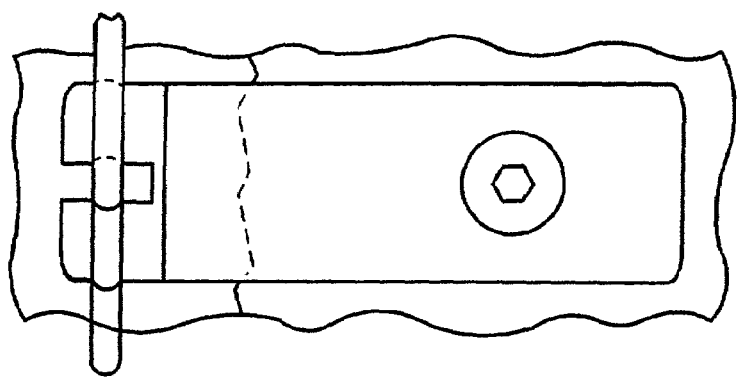
FIG. 20 is a plan view of FIG. 18.
Figure 19:
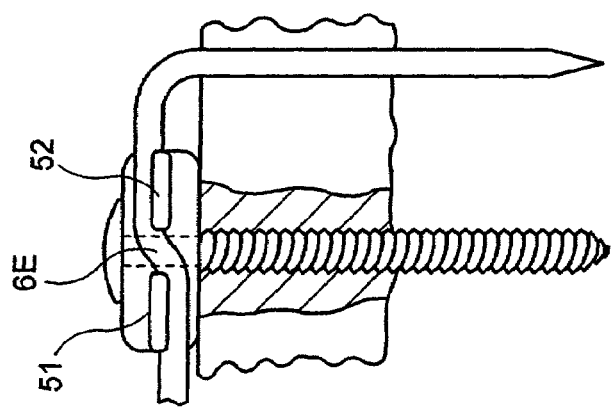
FIG. 19 is an end view of FIG. 18.
Figure 18:
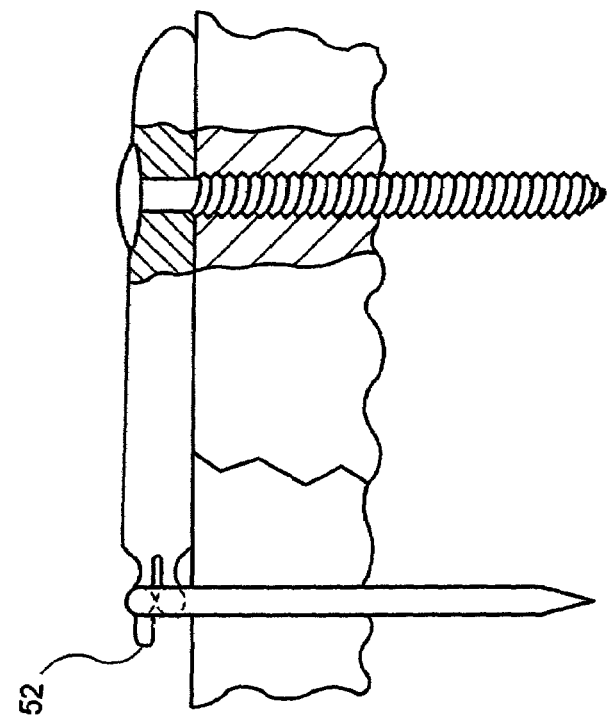
FIG. 18 shows a modified version of the embodiment shown in FIG. 15.

FIGS. 18–20 show a modification of the embodiment illustrated in FIGS. 15–17 in that the tabs 51 and 52 are placed at the same level and the pin is bent at 6E so as to be gripped from above and below by the tabs and be securely held in position thus being prevented from undergoing lateral displacement.

Figure 23:
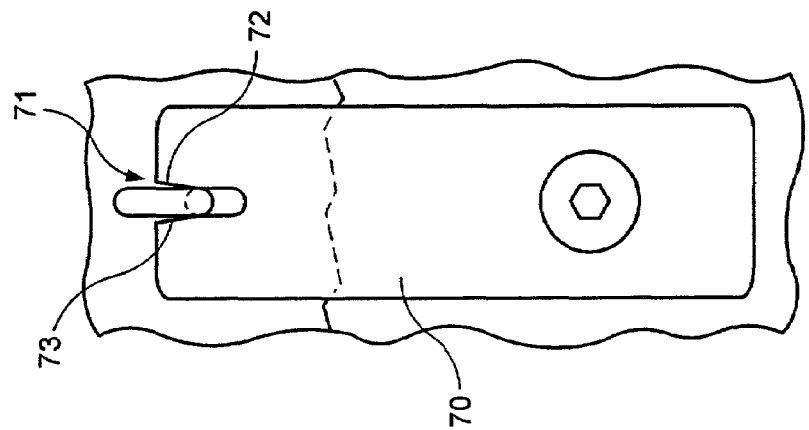
FIG. 23 is a plan view of FIG. 21.
Figure 22:
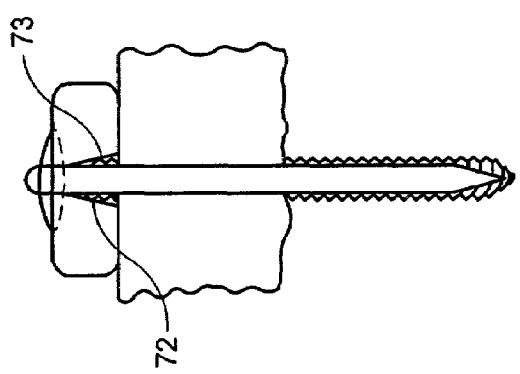
FIG. 22 is an end view of FIG. 21.
Figure 21:
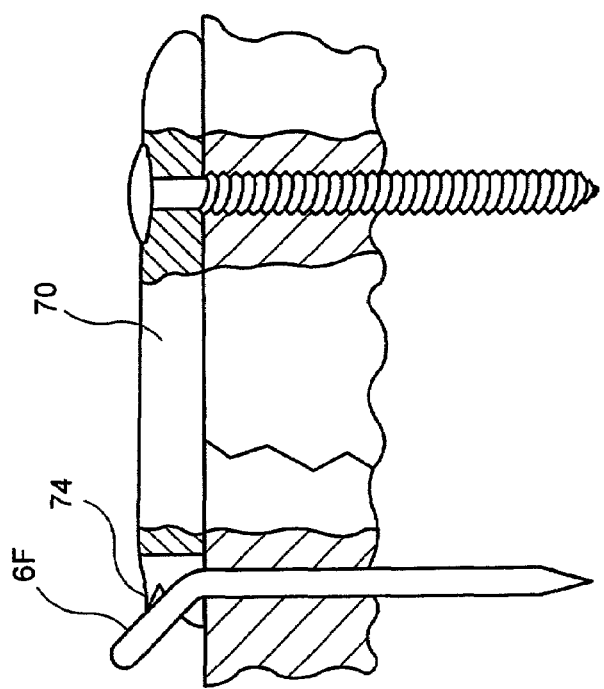
FIG. 21 shows another embodiment of engagement of the fixation plate and the K-wire.

FIGS. 21–23 show an embodiment in which the fixation plate 70 is formed at its end with a groove 71 which has side surfaces 72 and 73, which as viewed in FIG. 22, taper in narrowing manner from the lower surface of the fixation plate to the upper surface thereof. As seen in FIG. 23, the side surfaces 72 and 73 also narrow in a V-shape in a direction from the end of the fixation plate 70 inwardly thereof. When the bent portion 6F of the pin is inserted into the groove 71, it becomes locked therein as the plate 70 is screwed down. The bent portion 6F of the pin can be provided with a barb 74 to engage the fixation plate and lock the pin and further prevent the pin from backing out of the bone structure.

Figure 26:
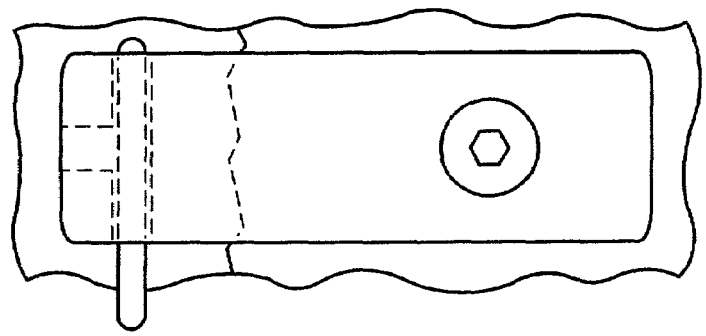
FIG. 26 is a plan view of FIG. 24.
Figure 25:
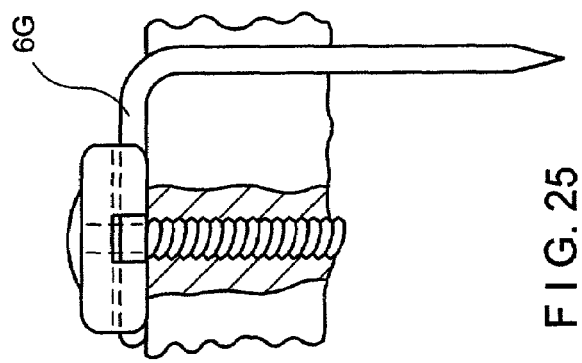
FIG. 25 is an end view of FIG. 24.
Figure 24:
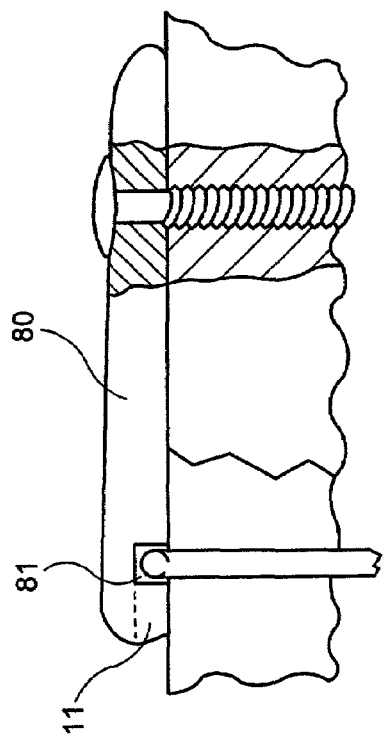
FIG. 24 shows another embodiment of engagement of the fixation plate and the K-wire.

FIGS. 24–26 illustrate a further embodiment in which fixation plate 80 is provided with a transverse groove 81 extending through the fixation plate to receive a transverse bend portion 6G of the fixation pin. In this embodiment, the fixation plate 80 is provided with transverse groove 81 as well as with longitudinal groove 11 to enable the fixation plate to be employed in the arrangement as shown in FIGS. 24–26 as well as in the arrangement shown in FIG. 7.

FIGS. 27–35 show several embodiments in which instead of bending an end of the pin and engaging the bent end by the fixation plate, the end of the pin is straight and it is secured to the fixation plate by crimping the fixation plate.

Figure 27:
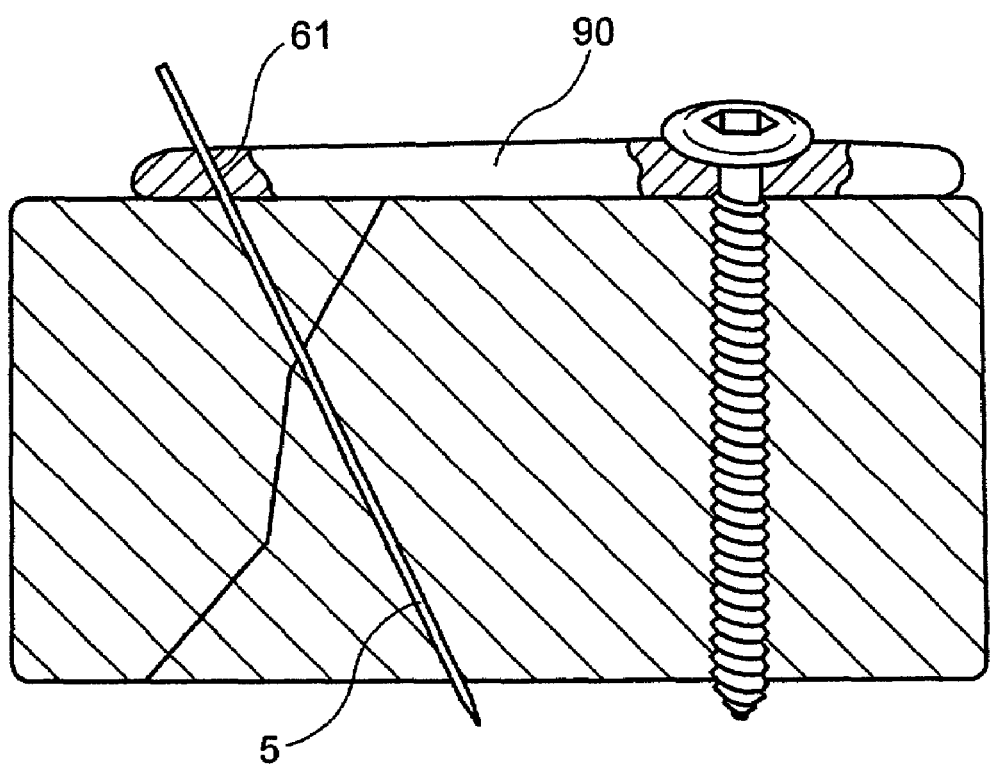
FIG. 27 is a side elevation view showing another embodiment of the fixation plate.

FIGS. 27 and 28 show a fixation plate 90 similar to those described earlier except that the plate has a bore 91 therein in which the fixation pin 5 is slidably engaged. The end of the pin is straight and not bent as in the previously described embodiments. In order to secure the pin 5 and prevent it from backing out of the bone structure or sliding in the plane of the plate a crimping tool 92 engages the plate 90 around the hole 91 and a crimping force F is applied to the plate 90 to deform the plate at crimps 93 and cause the hole 91 and pin 5 to be deformed and clamped together so that the pin is secured against backing out of the bone structure or sliding in the plane of the plate.

Instead of receiving the pin 5 in the hole 91 as shown in FIG. 27, the end of the plate 100 can be formed with an open groove 101 as shown in FIG. 30. Afer crimping, the legs 102 of the plate on both sides of the groove 101 are crimped against the pin 5 to clampingly secure the pin in place.

An alternative in either of the embodiments in FIG. 28 or FIG. 30 is to cut the pin at the level of the hole and weld the pin to the plate.

Figures 33, 34, 35:
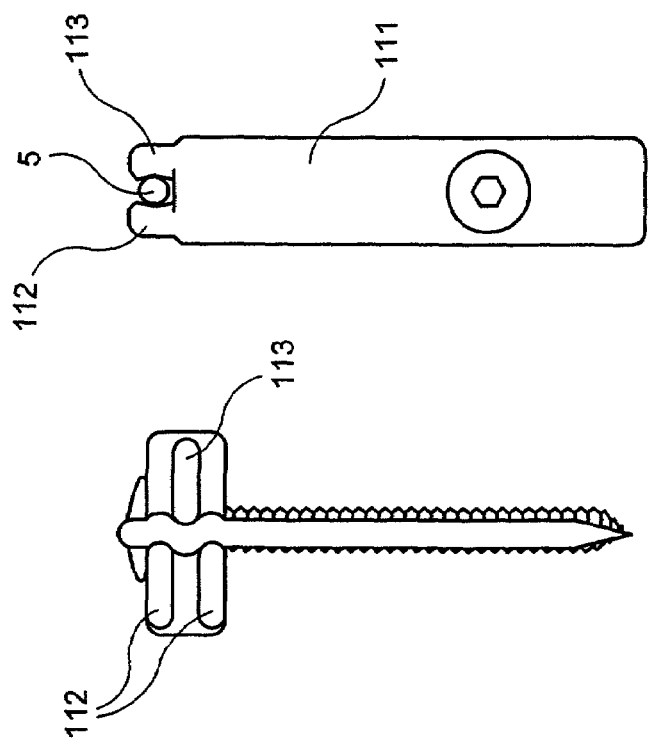
FIG. 33 is a plan view of FIG. 32.
FIG. 34 shows FIG. 32 after completion of assembly.
FIG. 35 is a plan view of FIG. 34.
Figure 32:
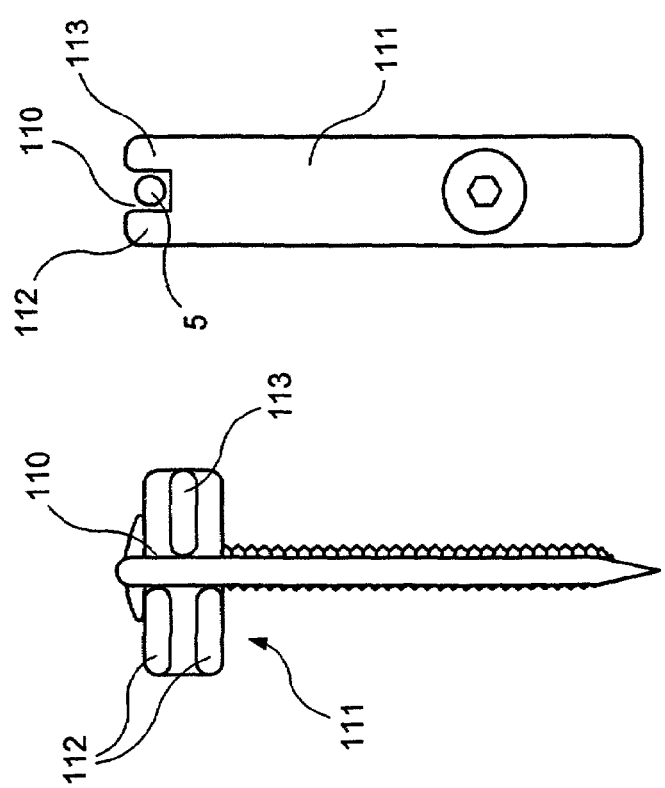
FIG. 32 is an end view of a modified embodiment of FIG. 16 in a preliminary stage of assembly of the pin and fixation plate.

In the embodiment shown in FIGS. 32–35, the pin 5 extends through a groove 110 in the end of a fixation plate 111. The end of the plate 111 is formed with longitudinally extending tabs 112, 113 defining the groove 110. The tabs 112, 113 straddle opposite sides of the pin 5. As seen in FIG. 32 two tabs 112 are arranged one above the other at one side of the pin 5 and one tab 113 is at the opposite side of the pin at a level between the tabs 112. After crimping, the tabs 112, 113 and pin 5 are deformed as shown in FIGS. 34 and 35 and the end of pin 5 is clampingly engaged with tabs 112, 113.

The invention has been described with reference to a number of embodiments adapted for use with pins for fixing unstable bone fragments to stable fragments. These embodiments solve the problem in the use of these pins due to bending migrating and backing out into the soft tissues. The embodiments of the invention serve to prevent bending and migration of a flexible pin as well as migration of the pin into the soft tissues.

Although the invention is disclosed with reference to particular embodiments thereof, it will become apparent to those skilled in the art that numerous modifications and variations can be made which will fall within the scope and spirit of the invention as defined by the attached claims.

What is claimed is:

1. A fixation device for fixing a fracture in a bone structure, said fixation device comprising:
    a bendable fixation pin adapted for penetrating through an unstable bone fragment of a bone structure across a fracture and into a stable bone fragment of said bone structure, said pin having an end extending out from said unstable bone fragment,
    a fixation plate adapted for being secured to the stable bone fragment at a distance from said end of said fixation pin,
    said fixation plate being engageable with said end of said bendable pin to prevent said pin from backing out of the bone structure while providing restraint against movement of said pin in the plane of the plate, said pin including a bent end portion which is bent at an angle so as to be adapted to be substantially parallel to a superficial surface of the bone structure, said fixation plate having a lower surface adapted to face the superficial surface of the bone structure when secured to the stable bone, said fixation plate being provided with a groove at said lower surface extending partially through the fixation plate for engaging said bent end portion of said pin to prevent the pin from backing out of the unstable bone fragment while providing the restraint of the pin for movement in the plane of the plate.

2. The fixation device as claimed in claim 1, wherein said bent portion of said pin is bent longitudinally of said fixation plate.

3. The fixation device as claimed in claim 1, wherein said bent portion of said pin is bent transversely of said fixation plate.

4. The fixation device as claimed in claim 1, wherein said groove in said fixation plate has a side opening to permit the bent portion of said pin to protrude therefrom.

5. The fixation device as claimed in claim 1, wherein said bent portion of said pin has a U-shape, said fixation plate having an outer surface with a further groove in which said bent portion of U-shape is gripped.

6. The fixation device as claimed in claim 1, wherein said fixation plate has an end with a groove therein, said groove having a V-shape in a longitudinal direction of the fixation plate and narrowing in a direction from an undersurface of said fixation plate to an outer surface of said fixation plate.

7. The fixation device as claimed in claim 1, wherein said pin has a smooth end for penetrating into said stable bone fragment.

8. The fixation device as claimed in claim 1, wherein said pin has a threaded end for threaded engaging in said stable bone fragment.

9. The fixation device as claimed in claim 1, wherein said bent end portion of said fixation pin has a length for extending a distance from its entry site into the unstable bone fragment, said groove in said fixation plate receiving said bent end portion of said pin.

10. The fixation device as claimed in claim 1, wherein said fixation plate has a hole in which said pin extends, said pin having a tip end which is cut in proximity to a top surface of the plate and is welded to said plate thereat.

11. The fixation device as claimed in claim 1, wherein said groove is dimensioned to accommodate said bent end portion of the pin upon placement of the fixation plate on the bone structure.

12. The fixture device as claimed in claim 11, wherein said groove has a rectangular cross section and extends in said fixation plate to an end thereof at which the groove opens outwardly of the plate.

13. A fixation device for fixing a fracture in a bone structure, said fixation device comprising:
   a bendable fixation pin adapted for penetrating through an unstable bone fragment of a bone structure across a fracture and into a stable bone fragment of said bone structure, said pin having an end extending out from said unstable bone fragment,
   a fixation plate adapted for being secured to the stable bone fragment at a distance from said end of said fixation pin,
   said fixation plate being engageable with said end of said bendable pin to prevent said pin from backing out of the bone structure while providing restraint against movement of said pin in the plane of the plate, wherein said end of said fixation pin includes a bent end portion which is engaged by said fixation plate to prevent said pin from backing out of the unstable bone fragment while providing restraint against movement of said pin in the plane of the plate, said fixation plate including means for engaging said bent end portion of said fixation pin, wherein said fixation plate has an end and said means on said fixation plate comprises two tabs extending longitudinally at said end in transversely spaced relation, said tabs facing one another to engage said bent portion of the pin from above and below.

14. The fixation device as claimed in claim 13, wherein said tabs are at different levels at said end of the fixation plate.

15. The fixation device as claimed in claim 13, wherein said tabs are at the same level at said end of the fixation plate and said bent portion of said pin is bent to pass between said tabs.

16. A fixation device for fixing a fracture in a bone structure, said fixation device comprising:
   a bendable fixation pin adapted for penetrating through an unstable bone fragment of a bone structure across a fracture and into a stable bone fragment of said bone structure, said pin having an end extending out from said unstable bone fragment,
   a fixation plate adapted for being secured to the stable bone fragment at a distance from said end of said fixation pin,
   said fixation plate being engageable with said end of said bendable pin to prevent said pin from backing out of the bone structure while providing restraint against movement of said pin in the plane of the plate, wherein said end of said fixation pin includes a bent end portion which is engaged by said fixation plate to prevent said pin from backing out of the unstable bone fragment while providing restraint against movement of said pin in the plane of the plate, said fixation plate including means for engaging said bent end portion of said fixation pin, wherein said means for engaging said bent portion of fixation pin comprises a groove in said plate for receiving said bent portion of said pin wherein said fixation plate has an end, said groove extending longitudinally in said fixation plate and being open at said end of said fixation plate.

17. The fixation device as claimed in claim 16, wherein said bent portion of said fixation pin is bent at a second bend to form a second bent portion, said fixation plate having a hole through which said second bent portion of said pin can extend.

18. A fixation device for fixing a fracture in a bone structure, said fixation device comprising:
   a bendable fixation pin adapted for penetrating through an unstable bone fragment of a bone structure across a fracture and into a stable bone fragment of said bone structure, said pin having an end extending out from said unstable bone fragment,
   a fixation plate adapted for being secured to the stable bone fragment at a distance from said end of said fixation pin,
   said fixation plate being engageable with said end of said bendable pin to prevent said pin from backing out of the bone structure while providing restraint against movement of said pin in the plane of the plate, said fixation plate including means for engaging said end of said fixation pin, wherein said means for engaging said end of said fixation pin comprises a groove in said plate for receiving said end of said pin, and a barb on said pin to engage said fixation plate when said pin is received in said groove.

19. A fixation device for fixing a fracture in a bone structure, said fixation device comprising:
   a bendable fixation pin adapted for penetrating through an unstable bone fragment of a bone structure across a fracture and into a stable bone fragment of said bone structure, said pin having an end extending out from said unstable bone fragment,
   a fixation plate adapted for being secured to the stable bone fragment at a distance from said end of said fixation pin,
   said fixation plate being engageable with said end of said bendable pin to prevent said pin from backing out of the bone structure while providing restraint against movement of said pin in the plane of the plate, wherein said end of said fixation pin includes a bent end portion which is engaged by said fixation plate to prevent said pin from backing out of the unstable bone fragment while providing restraint against movement of said pin in the plane of the plate, said fixation plate including means for engaging said bent end portion of said fixation pin, said means for engaging said bent end portion of said fixation pin being constituted by a lower surface of said fixation plate which bears against said bent end portion of said fixation pin from above to restrain said pin with respect to the bone structure.

20. A fixation device for fixing a fracture in a bone structure, said fixation device comprising:
   a bendable fixation pin adapted for penetrating through an unstable bone fragment of a bone structure across a fracture and into a stable bone fragment of said bone structure, said pin having an end extending out from said unstable bone fragment,
   a fixation plate adapted for being secured to the stable bone fragment at a distance from said end of said fixation pin,
   said fixation plate being engageable with said end of said bendable pin to prevent said pin from backing out of the bone structure while providing restraint against movement of said pin in the plane of the plate, wherein said fixation plate has longitudinally extending tabs at an end of said fixation plate defining a groove in which said end of the pin extends, said tabs being crimped against said end of the pin to be deformingly and clampingly engaged therewith.

21. The fixation device as claimed in claim 20, wherein said end of the pin passes in a bore in said fixation plate and said fixation plate is crimped at said bore.

22. The fixation device as claimed in claim 20, wherein two said tabs are disposed one above the other at one side of the pin and a further said tab is disposed at an opposite side of the end of the pin.

23. The fixation device as claimed in claim 22, wherein said further tab is at a level between said two tabs disposed one above the other.

24. A fixation device for fixing a fracture in a bone structure, said fixation device comprising:
  a bendable fixation pin adapted for penetrating through an unstable bone fragment of a bone structure across a fracture and into a stable bone fragment of said bone structure, said pin having an end extending out from said unstable bone fragment,
  a fixation plate adapted for being secured to the stable bone fragment at a distance from said end of said fixation pin,
  said fixation plate having a lower surface with a dimple therein for receiving said extending end of said bendable pin to prevent said pin from backing out of the bone structure while providing restraint against movement of said pin in the plane of the plate.

25. A method of fixing a fracture in a bone structure, said method comprising:
  inserting a fixation pin into a stable fragment of a bone structure across a fracture and leaving an end of the pin extending from an unstable fragment of the bone structure,
  providing a fixation plate having means for securing he fixation plate to said bone structure at a distance from the extending end of said fixation pin,
  bending said end of said fixation pin to provide a bent portion extending at an angle with respect to an axis of the pin so that the bent portion extends parallel to the bone structure,
  engaging said fixation plate with said bent portion of said pin to prevent said pin from backing out of the bone structure while providing restraint against movement of said pin in the plane of the plate, and
  securing the fixation plate to the bone structure.

26. A method of fixing a fracture in a bone structure said method comprising:
  inserting a fixation pin into stable fragment of a bone structure across a fracture and leaving an end of the pin extending from an unstable fragment of the bone structure,
  inserting the end of the pin through a hole in a fixation plate,
  securing the fixation plate to said bone structure at a distance from the extending end of said fixation pin,
  cutting said end of said fixation pin in proximity to a top surface of the fixation plate, and
  welding said end of the fixation pin and said fixation plate together to prevent said pin from backing out of the bone structure while providing restraint against movement of said pin in the plane of the plate.

27. The method as claimed in claim 26, wherein said fixation plate is formed with a groove therein at an end of the fixation plate said groove extending from a lower surface of the fixation plate partially through the thickness of the plate so that engagement of the fixation plate with the bent end of the pin is effected by placing the fixation plate on the bone structure to insert the bent end of the pin into the groove, whereby, when secured, the fixation plate blocks movements of the bent end of the pin.

* * * * *